United States Patent [19]

Gramm et al.

[11] Patent Number: 4,495,108

[45] Date of Patent: Jan. 22, 1985

[54] PROCESS FOR PREPARING DIALKYL PROPANEDIIMIDATE DIHYDROHALIDES

[75] Inventors: Jeffrey S. Gramm, Wilmington; Edwin L. Mongan, Jr., Newark, both of Del.; Patrick J. Sheeran, Landenberg, Pa.

[73] Assignee: E. I. Du Pont de Nemours and Company, Wilmington, Del.

[21] Appl. No.: 474,470

[22] Filed: Mar. 11, 1983

[51] Int. Cl.$^3$ ............................................. C07C 41/01
[52] U.S. Cl. ................................................. 260/453.7
[58] Field of Search ..................................... 260/453.7

[56] References Cited

U.S. PATENT DOCUMENTS 4,310,740 1/1982 Adams ............................... 260/453.7

OTHER PUBLICATIONS

Noller, Textbook of Organic Chemistry, 2nd Ed., W. B. Saunders Co., Philadelphia, 1958, p. 129.

*Primary Examiner*—Henry R. Jiles

[57] ABSTRACT

An improved process for preparing a dialkyl propanediimidate dihydrohalide by reacting malononitrile, an alcohol, and hydrogen halide, wherein the improvement comprises conducting the reaction under greater than atmospheric pressure in a halobenzene, haloalkylbenzene or alkylbenzene solvent.

15 Claims, No Drawings

PROCESS FOR PREPARING DIALKYL PROPANEDIIMIDATE DIHYDROHALIDES

BACKGROUND OF THE INVENTION

This invention relates to an improved process for preparing certain dialkyl propanediimidate dihydrohalides.

McElvain and Schroeder, JACS 71, 43 (1949), disclose the preparation of dimethyl and diethyl propanediimidate dihydrochloride by treating malononitrile and the corresponding alcohol with a large excess of hydrogen chloride using a chloroform-dioxane mixture and dioxane, respectively, as solvents. The process is disclosed to give high yields, but a reaction time of about twenty-four hours is required.

U.S. Pat. No. 4,310,740, issued on Jan. 12, 1982 to Adams, discloses an improved process for preparing a dialkyl propanediimidate dihydrohalide by reacting malononitrile, an alcohol and hydrogen halide in an alkyl acetate solvent.

Imido ester hydrohalides are well-known compounds. They are useful as chemical intermediates for other chemical compounds such as amidine hydrochlorides or as intermediates for herbicides as described in U.S. Pat. Nos. 4,287,343 and 4,229,960. Improvements in the process for preparing these imido ester hydrohalides, for example, improvement providing greater economy and ease of operation, are increasingly desirable.

SUMMARY OF THE INVENTION

An improved process for preparing dialkyl propanediimidate dihydrohalides of the formula:

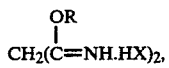

$$CH_2(C(OR)=NH \cdot HX)_2,$$

where
R = alkyl of 1 to 3 carbons, and
X = Cl or Br, has now been found. This new process involves contacting, at greater than atmospheric pressure, malononitrile, an alcohol ROH, where R is as defined above, and anhydrous hydrogen halide HX, where X is chlorine or bromine, in the presence of a halobenzene, haloalkylbenzene or alkylbenzene solvent having a boiling point in the range of about 100° to 200° C. at atmospheric pressure.

This new process offers a number of advantages over the previously known process described in U.S. Pat. No. 4,310,740 to Adams. The instant process can be run with greater ease due to the fact that the dialkyl propanediimidate dihydrohalide need not be isolated before use in certain subsequent reactions, and the solvent is easily recycled and gives less corrosive reaction mixtures when mixed with hydrogen halides than does methyl acetate. Additionally, in the preferred embodiment of the Adams process, the hydrohalic acid is used in an amount sufficient to saturate the solvent. In the preferred embodiment of the new process described and claimed herein, the hydrohalic acid is used in an excess of only thirty percent over the stoichiometric amount, thus conserving material and reducing waste disposal problems.

DETAILED DESCRIPTION OF THE INVENTION

The halobenzene, haloalkylbenzene or alkylbenzene solvents utilized in the improved process of this invention are liquids at room temperature and atmospheric pressure and have boiling points in the range of about 100° to 200° C. at atmospheric pressure. The terms halobenzene, alkylbenzene and haloalkylbenzene refer, respectively, to benzene substituted with one or more halogens, one or more alkyl groups or a combination thereof. Practically speaking, the benzene derivatives which are readily available and are suitable for use in this invention are those substituted with one or two chlorine atoms, with one bromine atom, with one to three methyl or ethyl groups, with one butyl group or with one metyl group as well as one or two chlorine atoms. The following are examples, not intended to be all-inclusive, of solvents within the scope of this invention.

| Solvent | Boiling Point (°C.) |
|---|---|
| m-xylene | 138 |
| o-xylene | 144 |
| p-xylene | 138.5 |
| toluene | 110.7 |
| chlorobenzene | 131.6 |
| m-dichlorobenzene | 172 |
| o-dichlorobenzene | 172–179 |
| m-chlorotoluene | 161.6 |
| o-chlorotoluene | 159.2 |
| p-chlorotoluene | 162–166 |
| dichlorotoluene | 200 |
| ethylbenzene | 136 |
| diethylbenzene | 179.8–184.8 |
| bromobenzene | 156.6 |
| sec-butylbenzene | 170.65 |
| tert-butylbenzene | 169.1 |
| mesitylene | 165 |

The preferred solvents for use in the process of this invention are xylenes, toluene, chlorobenzene, and dichlorobenzenes. Mixtures of suitable solvents can also be used.

In the process of this invention, about 2 to 3 molar equivalents, based on malononitrile, of alcohol are used. Preferably about 2 to 2.2, and more preferably about 2.2, molar equivalents of alcohol are used. About 2 to 4 molar equivalents, also based on malononitrile, of anhydrous hydrogen halide are used. Preferably about 2.2 to 3 molar equivalents of hydrogen halide are used.

The malononitrile concentration in the haloaryl, alkylaryl or haloalkylaryl solvent can vary from about 1 to 20 weight percent. A concentration of about 5 to 15 weight percent is preferred and 10 to 15 weight percent is more preferred.

The process is run at a temperature in the range of about 0° to 50° C., preferably about 10° to 30° C. and more preferably about 15° to 25° C. The reaction is run under greater than atmospheric pressure, generally under about 2 to 150 psig (pounds per square inch gauge), more preferably about 10 to 40 psig. When X = Cl, it is practical to run the reaction under HCl pressure and when X = Br it is practical to run the reaction under HBr pressure.

The order in which the reactants are contacted is not critical except that the malononitrile and the hydrogen halide are preferably not contacted in the absence of the alcohol. The reaction mixture should be agitated to insure that the malononitrile is thoroughly dispersed or dissolved in the solvent.

The process of this invention is further illustrated by the following examples, in which temperatures are in degrees centigrade and parts are by weight unless otherwise specified. These examples are provided to illustrate the process of this invention and should not be deemed as limiting the scope thereof.

EXAMPLE 1

Preparation of Dimethyl Propanediimidate Dihydrochloride

A mixture of 33 parts of malononitrile, 35 parts of methanol, and 346 parts of xylenes was stirred in a 1-L pressure vessel while anhydrous hydrogen chloride was introduced at a pressure of 20 psig. The mixture was stirred and held at 14° to 23° with cooling, and the HCl pressure was maintained at 20 psig until 55 parts of HCl were introduced (~2 hours). HCl feed was then discontinued and the reaction mass was stirred another 4 hours at 20° to 24°. The resulting slurry was filtered, and the solid product dried at room temperature to give 89 parts (88 percent weight yield based on malononitrile charged) of the title compound, which was identified by comparison with material produced as described in U.S. Pat. No. 4,310,740. The molar ratio of hydrogen chloride to malononitrile in this example is 2.6:1, compared to a ratio of 4.5:1 in Example 1 of U.S. Pat. No. 4,310,740.

EXAMPLE 2

Preparation of Dimethyl Propanediimidate Dihydrochloride and Its Use in a Subsequent Reaction Without Isolation A mixture of 58 parts of malononitrile, 62 parts of methanol and 433 parts of xylenes was stirred in a 1-L pressure vessel while anhydrous hydrogen chloride was introduced at a pressure of 25 psig. The mixture was stirred and held at 20° to 24° with cooling, and the HCl pressure was maintained at 25 psig until 83 parts of HCl were introduced (~1¼ hours). HCl feed was then discontinued and the reaction mass was stirred another 5 hours at 21°–22°, bottled under a N₂ blanket and stored overnight in a refrigerator.

The entire reaction mass was then transferred over a 15-minute period to a 1-L vessel containing a well-stirred mixture of 73 parts 50% aqueous cyanamide and 350 parts of water. During this addition, the reaction mixture was held below 10° by external cooling, and 50% aqueous sodium hydroxide was added as required to hold the pH between 5 and 7. The resulting slurry was warmed to room temperature, stirred for two hours and filtered. The solid product was washed with water and dried under a stream of nitrogen at room temperature to give 80 parts (58% yield based on malononitrile) of methyl 3-amino-3-methoxy-N-cyano-2-propeneimidate. The identity of this material was established by comparison with material produced by the procedure of U.S. Pat. No. 4,235,802.

This product was of sufficient purity for conversion to 2-amino-4,6-dimethoxypyrimidine as described in U.S. Pat. No. 4,299,960.

It was found that use of xylene solvent in this process was advantageous for several reasons. First, a uniform slurry of the diimidate is formed, thereby facilitating the transfer of the diimidate to the neutralization reactor. Second, the pH of the reaction mixture in the neutralization chamber is easy to control because of the density of the xylene solvent. Finally, because of the relatively high boiling point of the xylenes, little xylene is lost through vaporization during vacuum filtration of the final product, providing for easy solvent recovery.

Below is a table showing data for 5 runs in which dimethyl propanediimidate dihydrochloride was prepared in a 1-L pressure vessel as described in Example 1. The last row shows the yield to methyl 3-amino-3-methoxy-N-cyano-2-propeneimidate, corrected for purity, which was prepared in a 1-L vessel in accordance with Example 2. The temperature is in degrees Centigrade, pressure in psig, time in hours and yield in percent based on malononitrile charged.

| Ex. | Temp. Range | HCl Pressure | Rxn. Time | Molar Ratio to Malononitrile | | Pure Yield |
|---|---|---|---|---|---|---|
| | | | | Methanol | HCl | |
| 3 | 20–24 | 24 | 6.5 | 2.2 | 2.4 | 55 |
| 4 | 20–23 | 23 | 6.0 | 2.2 | 2.4 | 60 |
| 5 | 20–23 | 25 | 6.3 | 2.2 | 2.6 | 59 |
| 6 | 20–22 | 25 | 6.0 | 2.2 | 2.6 | 58 |
| 7 | 20–25 | 23 | 6.5 | 2.2 | 2.6 | 60 |

What is claimed is:

1. An improved process for preparing a dialkyl propanediimidate dihydrohalide of the formula:

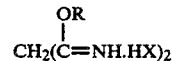

where
R is alkyl of 1 to 3 carbon atoms, and
X is chlorine or bromine,
by reacting malononitrile, an alcohol ROH and anhydrous hydrogen halide HX, wherein the improvement comprises conducting the reaction under a pressure of about 2 to 150 psig in a halobenzene, haloalkylbenzene or alkylbenzene solvent having a boiling point in the range of about 100° to 200° C. at atmospheric pressure.

2. The process of claim 1 where the solvent is selected from one or more of the following: o-xylene, m-xylene, p-xylene, toluene, chlorobenzene, m-dichlorobenzene or o-dichlorobenzene.

3. The process of claim 2 where the solvent is o-, m- or p-xylene or mixtures thereof.

4. The process of any of claims 1 to 3 where the reaction is conducted under pressure of about 10 to 40 psig.

5. The process of any of claims 1 to 3 where the reaction is conducted at a temperature in the range of about 0° to 50° C.

6. The process of claim 5 where the reaction is conducted at a temperature of about 10° to 30° C.

7. The process of claim 6 where the reaction is conducted at a temperature of about 15° to 25° C.

8. The process of any of claims 1 to 3 where about 2 to 3 moles of alcohol ROH are present per mole of malononitrile.

9. The process of claim 8 where about 2.2 moles of alcohol ROH are present per mole of malononitrile.

10. The process of any of claims 1 to 3 where about 2 to 4 moles of hydrogen halide HX are present per mole of malononitrile.

11. The process of claim 10 where about 2.2 to 3 moles of hydrogen halide HX are present per mole of malononitrile.

12. The process of any of claims 1 to 3 where the concentration of the malononitrile in the halobenzene, alkylbenzene or haloalkylbenzene solvent is in the range of about 1 to 20 weight percent.

13. The process of claim 12 where the concentration of the malononitrile in the halobenzene, alkylbenzene or haloalkylbenzene solvent is in the range of about 10 to 15 weight percent.

14. The process of any of claims 1 to 3 where R=CH$_3$.

15. The process of any of claims 1 to 3 where X=Cl.